US00PP14196P29

(12) United States Plant Patent
Bradford

(10) Patent No.: US PP14,196 P2
(45) Date of Patent: Sep. 30, 2003

(54) PLUM TREE NAMED 'PLUMSWEETTWO'

(50) Latin Name: *Prunus salicina*
Varietal Denomination: 'PLUMSWEETTWO'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,614

(22) Filed: Nov. 21, 2002

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick

(57) ABSTRACT

The present invention relates to a plum tree, *Prunus salicina*, and more particularly to a new and distinct variety broadly characterized by a large size, vigorous, hardy, heavy blooming, moderately productive and self-unfruitful tree, that may be cross pollinized by 'August Yummy®' (U.S. Plant patent application Ser. No. 10/300,603 filed concurrently). The fruit matures under the ecological conditions described during the third week in July, with first picking on Jul. 20, 2002. The fruit is uniformly medium in size, full dark purplish red in skin color, clingstone in type, red in flesh color, very firm and crisp in texture, very good in flavor, and holds well in cold storage for more than thirty days. The variety was developed as a first generation cross using an unnamed plum seedling as the selected seed parent and 'Black Noble' (U.S. Plant Pat. No. 7,504) as the selected pollen parent.

1 Drawing Sheet

Botanical classification: *Prunus salicina*.
Variety denomination: 'PLUMSWEETTWO'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'PLUMSWEETTWO'. The present variety was hybridized by me in 1996, germinated and grown as a seedling on its own root in my greenhouse, and upon reaching dormancy transplanted to a cultivated area of my experimental orchard at Bradford Farms near Le Grand, Calif. in Merced County (San Joaquin Valley). Specifically, the variety was developed as a first generation cross using an unnamed plum seedling as the selected seed parent and 'Black Noble' (U.S. Plant Pat. No. 7,504) as the selected pollen parent. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its pollen parent, 'Red Noble' (U.S. Plant Pat. No. 7,504), by being self-unfruitful and by producing plums that are dark purplish red in skin color, very firm and crisp in texture, clingstone in type, and almost full red in flesh color, but is very distinguished therefrom and an improvement thereon by producing plums that are considerably larger in size, that are sweeter in flavor, and that mature about 40 days later.

SUMMARY OF VARIETY

The present plum variety is characterized by a large size, vigorous, hardy, and moderately productive tree. Being self-unfruitful, the present variety requires cross pollinization from another plum that blooms during the mid season, such as 'August Yummy®' (U.S. Plant patent application Ser. No. 10/300,603, filed concurrently). The fruit matures under the ecological conditions described during the third week in July, with first picking on Jul. 20, 2002. The fruit is uniformly medium in size, full dark purplish red in skin color, clingstone in type, red in flesh color, very firm and crisp in texture, very good in flavor, and holds well in cold storage for more than thirty days.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Jul. 25, 2002, on the original tree during its sixth growing season. All major color code designations are by reference to the Inter-Society Color Council, National Bureau of Standards. Common color names are also used occasionally.

TREE

Size: Large, reaching and maintaining a height of 12' [3.7 m.] and a spread of 10' [3.1 m.] after six growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Spreading and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Productive, thinning usually necessary.
Fertility: Self-unfruitful, requiring cross pollination by a suitable mid seasonal blooming plum, such as 'August Yummy®' (U.S. Plant patent application Ser. No. 10/300, 603 filed concurrently).
Bearing: Uncertain, especially if inclement weather is encountered during the blooming period.
Trunk:
*Size.*—Medium, reaching a maximum diameter of 4" [102 mm.] after the sixth growing season.
*Texture.*—Shaggy.
*Bark color.*—Dark grayish reddish brown [47. d.gy.rBr] with Grayish brown [61. gy.Br] crevices streaked throughout.
*Lenticels.*—Approximate Number Per Square Inch: 16. Color: Moderate orange [53. m.O]. Typical Size: ⅛" to ⅜" [3.2–9.5 mm.].
Branches:
*Size.*—Diameter of limb is 1¼" [32 mm.] measured 12" above the secondary fork, typical of *Prunus salicina*, and dependent upon cultural practices and climatic conditions.
*Texture.*—Smooth on first year wood, rough on second, shaggy thereafter.
*Color.*—1st Year Wood Topside: Moderate brown [58. m.Br] when exposed to sunlight. 1st Year Wood Underside: Strong yellow green [117. s.YG]. Older Wood: Moderate brown [57. m.Br].
*Lenticels.*—Approximate Number Per Square Inch: 50. Color: Moderate orange yellow [71. m.OY]. Typical size: 1/32" to ⅛" [0.8–3.2 mm.].
Leaves:
*Size.*—Large. Average Length: 4" [102 mm.]. Average width: 2 3/16" [56 mm.].
*Arrangement.*—Alternate.
*Thickness.*—Medium.
*Form.*—Elliptical.
*Apex.*—Acuminate.
*Base.*—Acute with an average angle base angle of 80 degrees.
*Surface.*—Smooth.
*Color.*—Dorsal Surface: Dark yellowish green [137. d.yG]. Ventral Surface: Moderate yellowish green [136. m.yG].
*Margin.*—Finely serrate.
*Venation.*—Pinnately net veined.
*Petiole.*—Average Length: ½" [12.7 mm.]. Average Thickness: 1/16" [1.6 mm.]. Color: Brilliant yellow green [116. brill.YG] becoming Dark red [16. d.R] with exposure to sunlight.
*Stipules.*—Number: 2 per leaf, up to 6 per growing tip. Average Length: 7/16" [11.1 mm.]. Color: Light yellow green [119. l.YG] with Dark grayish reddish brown [47. d.gy.rBr] tinging with age.
*Glands.*—Number: 1 to 5. Position: Both alternately and oppositely positioned on the petiole and base of blade. Size: Small. Form: Globose. Color: Light yellow green [119. l.YG] when young becoming Moderate reddish brown [43. m.rBr] with age.
*Leaf buds.*—Conic.

Flower buds:
*Hardiness.*—Hardy, with respect to central California winters.
*Diameter.*—Typically 3/16" [4.8 mm.] 1 week before bloom.
*Length.*—Typically ⅜" [9.5 mm.] 1 week before bloom.
*Form.*—Not appressed.
*Surface.*—Pubescent.
*Color.*—White [263. White].
Flowers: Perfect, complete, perigynous, usually a single pistil, typically thirty or more stamens, five sepals and petal locations alternately positioned.
*Average flower diameter.*—⅝" [15.9 mm.].
*Number of petals.*—Five, no double blossoms observed.
*Petal shape.*—Oval.
*Petal margin.*—Slightly wavy,
*Average petal diameter.*—5/16" [7.9 mm.].
*Average petal length.*—⅜" [9.5 mm.].
*Petal apex.*—Rounded.
*Petal base.*—Rounded.
*Petal color.*—White [263. White].
*Anther color.*—Pale yellow [89. p.Y].
*Stigma color.*—Light greenish yellow [101. l.gY].
*Sepal color.*—Brilliant yellow green [116. brill.YG].
*Sepal length.*—5/32" [4.0 mm.].
*Sepal width.*—3/32" [2.4 mm.].
*Average pistil length.*—5/16" [7.9 mm.].
*Average stamen length.*—5/16" [7.9 mm.].
*Fragrance.*—Moderate.
*Pollen production.*—Light to moderate.
*Blooming period.*—Medium compared with other varieties, two days after 'Santa Rosa' (unpatented).
*Onset of bloom.*—One percent on Feb. 24, 2002.
*Date of full bloom.*—Mar. 5, 2002.
*Duration of bloom.*—One to two weeks, dependent on ambient temperature.
*Number per cluster.*—Average 5, up to 10 observed.

FRUIT

Maturity when described: Firm ripe, Jul. 25, 2002.
Date of first picking: Jul. 20, 2002.
Date of last picking: Jul. 30, 2002.
Size: Uniform, medium.
*Average diameter axially.*—2 3/16" [55.6 mm.].
*Average diameter across suture plane.*—2½" [63.5 mm.].
*Typical weight.*—4.6 ounces [130 grams].
Form: Uniform, symmetrical, globose to slightly oblate.
*Longitudinal section form.*—Elliptical, compressed axially.
*Transverse section through diameter.*—Circular.
Suture: A very shallow groove extending from the base to just beyond the apex with a slight depression just after the pistil point.
Ventral surface: Rounded.
Lips: Virtually none to very slight.
Cavity: Flaring, circular, suture showing on one side.
*Depth.*—⅜" [9.5 mm.].
*Breadth.*—⅞" [22.2 mm.].
Base: Truncate, but slightly cuneate when viewed along the suture.
Apex: Truncate to rounded.
Pistil point: An inconspicuous dot.

Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to flesh.
*Astringency.*—Moderate.
*Tendency to crack.*—None observed in dry season.
*Color.*—Very dark purplish red [260. v.d.pR] smoothly blending to Dark purplish red [259. d.pR] with ample Light orange yellow [70. l.OY] freckling throughout, except along the suture.
*Bloom.*—Abundant.
Flesh:
*Color.*—Deep reddish orange [36. deep rO] becoming Very deep red [14. v.deep R] near the skin and stone.
*Surface of pit cavity.*—Covered with Dark red [16. d.R] fibers that break when strongly twisted from the stone.
*Amygdalin.*—Moderate.
*Juice.*—Very abundant, rich.
*Texture.*—Very firm, crisp.
*Fibers.*—Abundant, fine.
*Ripens.*—Fairly even.
*Flavor.*—Acidic and very sweet, typically 21 to 23 brix.
*Aroma.*—Slight.
*Eating quality.*—Very good.

STONE

Type: Clingstone.
Form: Oval.
Hilum: Narrow.
Base: Straight.
Apex: Acute, with an average angle of 90 degrees.
Sides: Equal.
Surface: Rough, with no grooves or fins.
External color of stone: Moderate reddish brown [43. m.rBr].
Pit wall color when cracked: Strong yellowish brown [74. s.yBr].
Cavity surface color: Moderate brown [58. m.Br].
Average pit wall thickness: 3/32" [2.4 mm.].
Average width: 3/4" [19.1 mm.].
Average length: 1 1/16" [27.0 mm.].
Average breadth: 3/8" [9.5 mm.].
Tendency to split: Very slight.
Kernel:
*Form.*—Oval.
*Pellicle color.*—Light grayish brown [60. l.gy.Br].
*Skin color.*—Pale yellow [89. p.Y] when freshly removed.
*Taste.*—Bitter.
*Viable.*—Yes.
*Average width.*—3/8" [9.5 mm.].
*Average length.*—5/8" [15.9 mm.].
*Amygdalin.*—Abundant.

USE

Market: Fresh market and long distance shipping.
Keeping quality: Excellent. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to its pollen parent, 'Red Noble' (U.S. Plant Pat. No. 7,504), by being self-unfruitful and by producing plums that are dark purplish red in skin color, very firm and crisp in texture, clingstone in type, and almost full red in flesh color, but is distinguished therefrom and an improvement thereon by producing plums that are considerably larger in size, that are sweeter in flavor, and that mature about 40 days later.

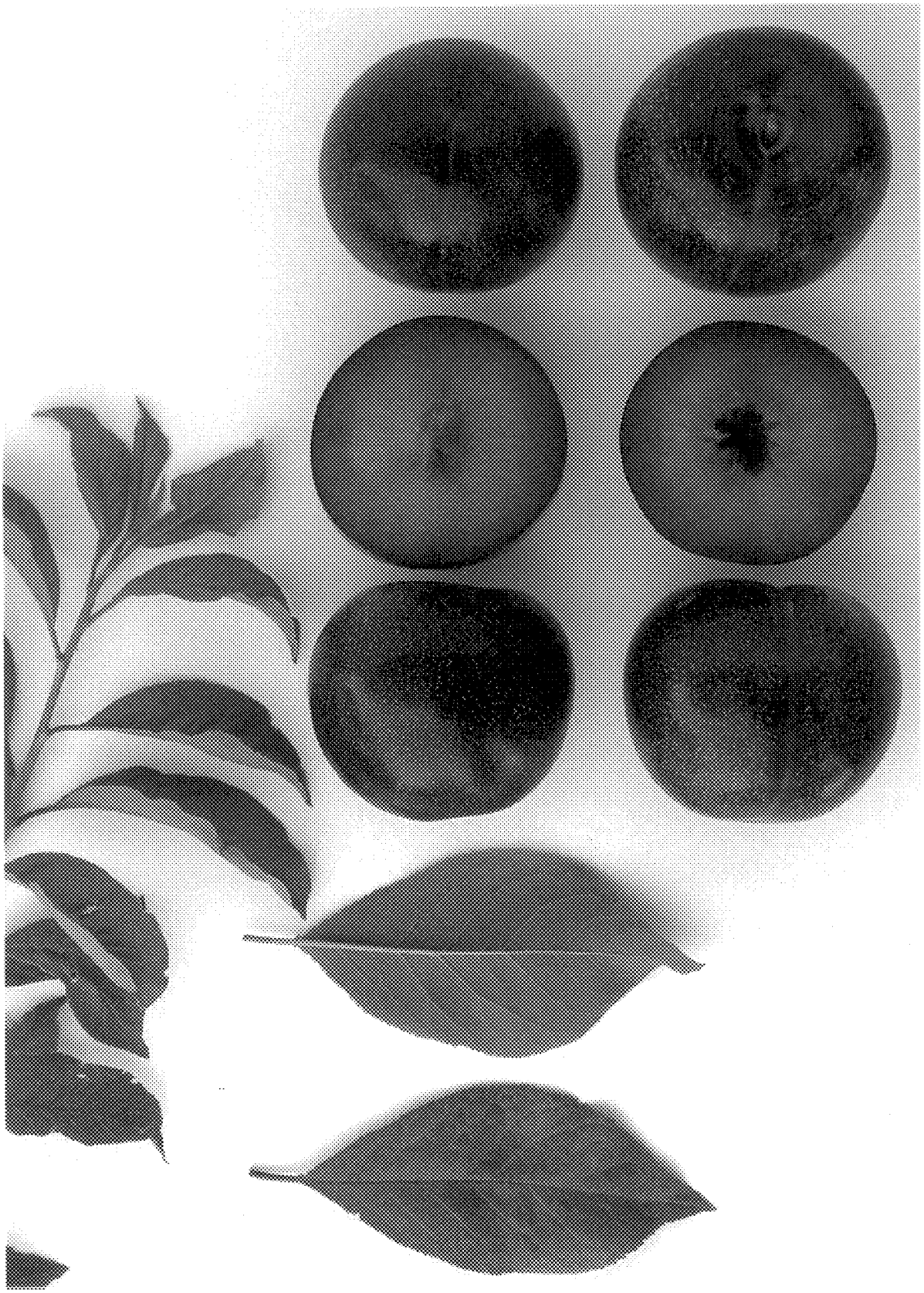

* * * * *